(12) United States Patent
Zajdowicz et al.

(10) Patent No.: US 8,669,069 B2
(45) Date of Patent: Mar. 11, 2014

(54) PROCUREMENT EXTRACTION BAG

(75) Inventors: Jan Zajdowicz, Aurora, CO (US); Todd Huft, Highlands Ranch, CO (US)

(73) Assignee: Allosource, Centennial, CO (US)

( * ) Notice: Subject to any disclaimer, the term of this patent is extended or adjusted under 35 U.S.C. 154(b) by 0 days.

(21) Appl. No.: 13/428,203

(22) Filed: Mar. 23, 2012

(65) Prior Publication Data

US 2013/0252269 A1      Sep. 26, 2013

(51) Int. Cl.
  *C12Q 1/02*     (2006.01)
  *C12N 5/00*     (2006.01)
  *C12M 1/00*     (2006.01)

(52) U.S. Cl.
  USPC ............................ 435/29; 435/325; 435/283.1

(58) Field of Classification Search
  USPC ........................................ 435/29, 325, 283.1
  See application file for complete search history.

(56) References Cited

U.S. PATENT DOCUMENTS

| 4,206,770 | A | 6/1980 | Ozgener |
| 6,247,619 | B1* | 6/2001 | Gill et al. ..................... 222/105 |
| 8,365,941 | B2* | 2/2013 | Mayer ........................ 220/259.3 |

* cited by examiner

*Primary Examiner* — Karen Cochrane Carlson
*Assistant Examiner* — Natalie Moss
(74) *Attorney, Agent, or Firm* — James A. Sheridan; Sheridan Law, LLC

(57) ABSTRACT

There is disclosed a method of procuring allograft tissue. In an embodiment, the method includes inserting an allograft through an opening into a procurement extraction container, sealing the opening, adding extraction fluid through a second opening, agitating the fluid, collecting the fluid for detection of contamination, and sealing the second opening. There is disclosed a procurement extraction container. In one embodiment, the container includes a wall defining an interior to receive the allograft, an opening into the interior, sized to receive the allograft, a closure device for the opening, the closure device providing a hermetic seal, a second opening providing a second passageway into the interior, the second opening having a connector interface and a second closure device providing a hermetic seal so as to provide, with the first closure and the at least one wall, a sterile barrier. Other embodiments are also disclosed.

12 Claims, 3 Drawing Sheets

PROCUREMENT EXTRACTION BAG

BACKGROUND

Generally, allograft tissue is swab tested during collection to determine bioburden presence. Typically, swabs are inoculated into a liquid growth medium to determine "growth" or "no growth." Thus, swabs are utilized to "qualitatively" show microorganism presence. Bioburden relates to the degree of microbial contamination or microbial load, i.e., the number of microorganisms contaminating an object. After contact with a swab during swab testing, the allograft tissue is placed in a procurement bag or other suitable container to prevent future contamination of the allograft tissue. The swab is preserved for future testing. However, swab testing merely tests a surface of the allograft tissue. Swabs are generally swabbed across the entire allograft surface; however, the sensitivity of the swab is poor. Other testing procedures are typically too difficult to carry out during the procurement process. Lack of equipment, cost of equipment, skill required to operate equipment, and size of equipment for other types of bioburden level testing force many technicians to utilize straightforward swab testing rather than other testing techniques.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an embodiment, there is provided a method of procuring an allograft tissue, the method comprising inserting an allograft tissue through a first opening into a procurement extraction container; sealing the first opening of the procurement extraction container; adding an extraction fluid from an extraction solution bottle through a second opening into the procurement extraction container; agitating the extraction fluid within the procurement extraction container; collecting the extraction fluid into the extraction solution bottle from the procurement extraction container for detection of contamination; and sealing the second opening of the procurement extraction container.

In another embodiment, there is provided a procurement extraction container for procuring an allograft tissue and detection of contamination in the allograft tissue, the procurement extraction container comprising at least one wall defining an interior sized to receive an allograft tissue; a first opening providing a first passageway between the interior and an external environment, the first opening sized to receive therethrough the allograft tissue from the external environment into the interior; a first closure device in operable connection with the first opening, the first closure device providing a hermetic seal at the first opening so as to provide, with the at least one wall, a sterile barrier for procurement of the allograft tissue disposed within the interior; a second opening providing a second passageway between the interior and the external environment, and the second opening having a connector interface; and a second closure device in operable connection with the connector interface of the second opening, the second closure device providing a hermetic seal at the second opening so as to provide, with the first closure and the at least one wall, the sterile barrier for procurement of the allograft tissue disposed within the interior.

In yet another embodiment, there is provided a kit for procurement of an allograft tissue, the kit comprising an extraction solution bottle having screw threads and a selectively removable cap having screw threads corresponding to the screw threads of the extraction solution bottle; a procurement extraction container comprising at least one wall defining an interior sized to receive an allograft tissue; a first opening providing a first passageway between the interior and an external environment, the first opening sized to receive therethrough the allograft tissue from the external environment into the interior; a first closure device in operable connection with the first opening, the first closure device providing a hermetic seal at the first opening so as to provide, with the at least one wall, a sterile barrier for procurement of the allograft tissue disposed within the interior; a second opening providing a second passageway between the interior and the external environment, and the second opening having a connector interface; and a second closure device in operable connection with the connector interface of the second opening, the second closure device providing a hermetic seal at the second opening so as to provide, with the first closure and the at least one wall, the sterile barrier for procurement of the allograft tissue disposed within the interior; extraction fluid initially disposed in the extraction fluid bottle; wherein the extraction solution bottle and the procurement extraction container selectively connect with one another to form a fluid connection with a hermetic seal with one another to provide the extraction fluid to the procurement extraction container and subsequently receive the extraction fluid from the container after contacting the allograft tissue disposed within the procurement extraction container; and wherein each of the extraction solution bottle and the procurement extraction container provide the sterile barrier for procurement of the extraction fluid and the allograft tissue, respectively.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Figure 1:
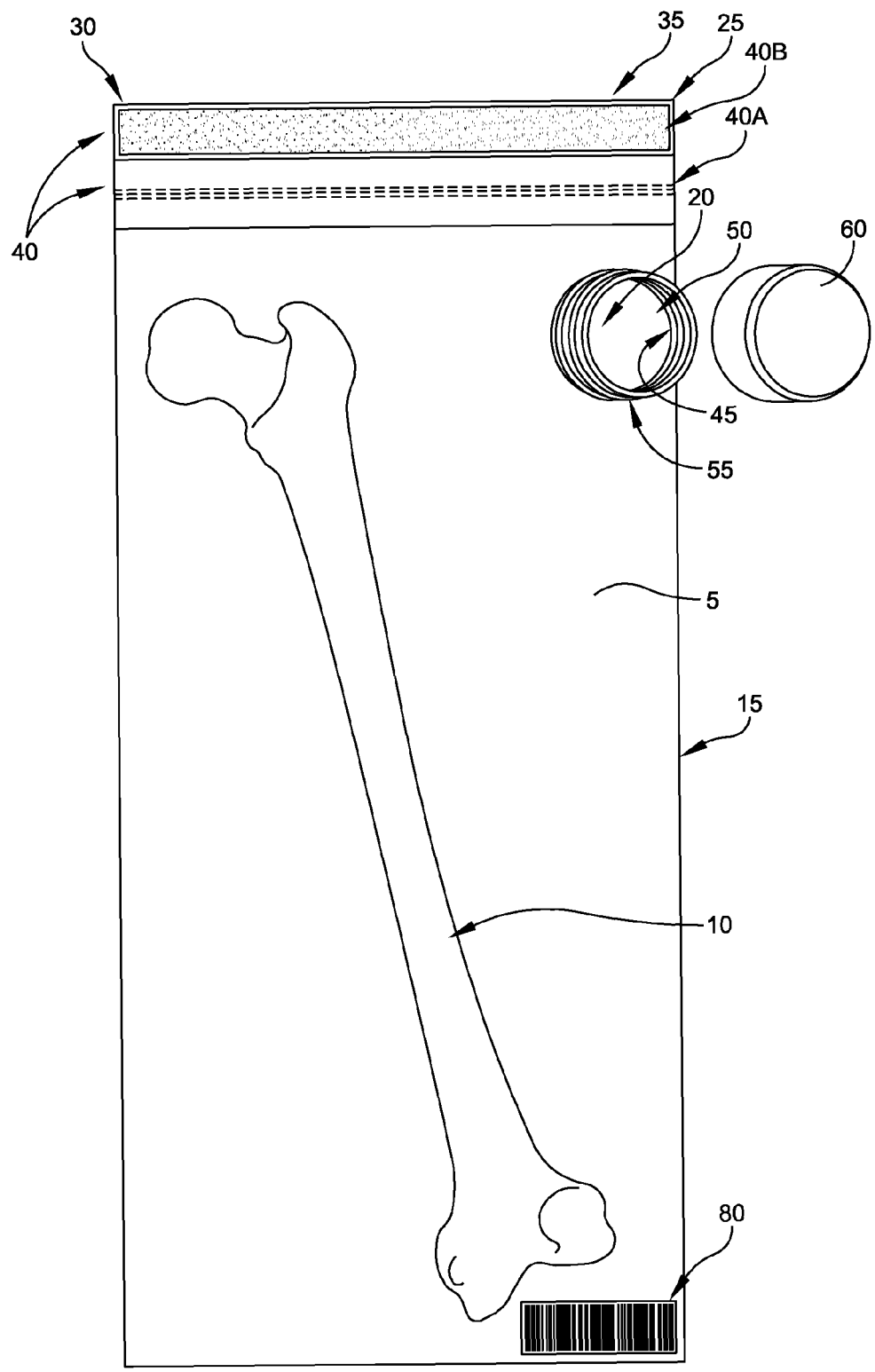
FIG. 1 illustrates a procurement extraction bag or container including an allograft bone.

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

In an embodiment, there is provided a method of procuring an allograft tissue. One method may include inserting an allograft tissue through a first opening into a procurement extraction container. The method may further include sealing the first opening of the procurement extraction container. The method may include adding an extraction fluid from an extraction solution bottle through a second opening into the procurement extraction container. The method may include the step of agitating the extraction fluid within the procurement extraction container. The method may include collecting the extraction fluid into the extraction solution bottle from the procurement extraction container for detection of contamination. The method may include the step of sealing the second opening of the procurement extraction container.

In one embodiment, the step of sealing the first opening includes forming a resealable seal with a zip-lock closure. In an embodiment, the step of sealing the first opening may include forming a non-resealable seal with a glue bar so as to provide a one-time closure. In another embodiment, the step of sealing the first opening may include forming a seal with a zip-lock closure and subsequently forming a non-resealable seal with a glue bar so as to provide a one-time closure.

In an embodiment, the step of adding the extraction fluid includes attaching the procurement extraction container and the extraction solution bottle to one another to form a hermetically sealed passageway so as to provide movement of the extraction fluid in a controlled manner between the extraction solution bottle and the procurement extraction container.

The step of agitating the extraction fluid may include shaking the procurement extraction container so as to liberate bioburden into the extraction fluid. Agitation may also include other mixing or movement inducing actions, e.g., squeezing, rolling, or other suitable actions.

The step of collecting the extraction fluid may include inverting the procurement extraction container to direct the extraction fluid into the extraction solution bottle. The step of collecting the extraction fluid may also include attaching a screw cap to the extraction solution bottle for transportation prior to detection of contamination.

The extraction solution bottle may be sealed with the extraction fluid and sent to a testing laboratory. The sealed bag with the allograft may be sent to a tissue bank. This minimizes the amount of time and effort needed to process the allograft and provides testing based on a test initiated at collection.

The step of sealing the second opening may include attaching a screw cap on the procurement extraction container.

Figure 2:
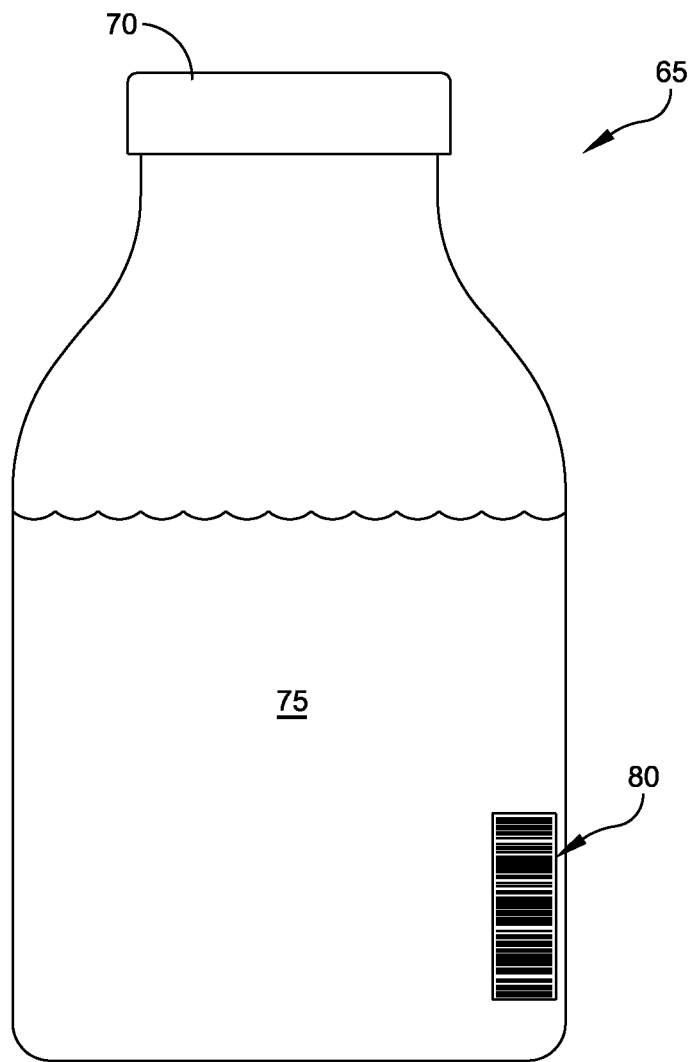
FIG. 2 illustrates an exemplary embodiment of an extraction solution bottle.

With general reference to FIGS. 1 and 2, and in an embodiment, a procurement extraction container 5 may be provided for procuring an allograft tissue 10 and detection of contamination in the allograft tissue 10. The procurement extraction container 5 may include at least one wall 15 defining an interior 20 sized to receive the allograft tissue 10. A first opening 25 in the container 5 provides a first passageway 30 between the interior 20 and an external environment 25. The first opening 25 may be sized to receive therethrough the allograft tissue 10 from the external environment 35 into the interior 20. A first closure device 40 may be in operable connection with the first opening 25. The first closure device 40 may provide a hermetic seal at the first opening 40. This provides, with the wall 15 (or walls 15), a sterile barrier for procurement of the allograft tissue 10 disposed within the interior 20.

A second opening 45 provides a second passageway 50 between the interior 20 and the external environment 35. The second opening 45 may have a connector interface 55.

A second closure device 60 may be in operable connection with the connector interface 55 of the second opening 45. The second closure device 60 may provide a hermetic seal at the second opening 45. This provides, with the first closure 40 and the wall 15 (or walls 15), the sterile barrier for procurement of the allograft tissue 10 disposed within the interior 20.

In an embodiment, the connector interface 55 may include screw threads rotatably engageable with a bottle 65 containing an extraction fluid. The connector interface 55 may be rotatably engageable with the second closure device 60. In one embodiment, the second closure device 60 is a screw cap.

In an embodiment, the wall 15 (or walls 15) may include a flexible sheet of material. In one embodiment, the flexible sheet of material forms a plastic bag.

In an embodiment, the first closure device 40 includes a zip-lock closure 40A. In another embodiment, the first closure 40 includes a glue bar 40B. In one embodiment, the glue bar 40B includes a non-resealable glue so as to provide a one-time closure. With this configuration, the wall 15 must be cut or the first closure 40 must be destructively opened to access the allograft tissue 10. This preserves the state of the bioburden on the allograft tissue 10 as tested with the extraction fluid. In another embodiment, the first closure 40 may include both a zip-lock closure 40A and a glue bar 40B together with one another.

The connector interface 55 of the second opening 45 may be a port configured for selective connection with an existing extraction solution bottle 65 (see FIG. 2.)

In an embodiment, the interior 20 is sized to receive the allograft tissue 10, which is a bone, together with a suitable volume of extraction fluid 75 to allow a non-destructive extraction test to detect contamination of the allograft tissue 10.

In one embodiment, the interior 20 is sized to receive the allograft tissue 10, which is a soft tissue graft, together with a suitable volume of extraction fluid 75 to allow a non-destructive extraction test to detect contamination of the allograft tissue 10.

Referring again to FIGS. 1 and 2, a kit may be provided for procurement of an allograft tissue. The kit may include the extraction solution bottle 65 having screw threads and a selectively removable cap 70 having screw threads corresponding to the screw threads of the extraction solution bottle 65. The kit may also include the procurement extraction container 5. The kit may include extraction fluid 75 initially disposed in the extraction fluid bottle 65. The extraction solution bottle 65 and the procurement extraction container 5 may selectively connect with one another to form a fluid connection with a hermetic seal with one another to provide the extraction fluid 75 to the procurement extraction container 5 and subsequently receive the extraction fluid 75 from the container 5 after contacting the allograft tissue 10 disposed within the procurement extraction container 5. Each of the extraction solution bottle 65 and the procurement extraction container 5 provide the sterile barrier for procurement of the extraction fluid 75 and the allograft tissue 10, respectively.

In one embodiment, the procurement extraction container 5 is a flexible bag, which may be wrapped around the extraction solution bottle 65 prior to insertion on the extraction bottle 65, prior to insertion of the allograft tissue 10 therein. The procurement extraction container 5 and the extraction solution bottle 65 may each have an identifier corresponding to one another.

In an embodiment, a barcode 80 may be provided on extraction solution bottle 65 and procurement extraction container 5. Additional stickers or other preprinted labels with barcode 80 may be provided with a unique identification number in the kit for procurement agency paperwork. In an embodiment, stickers with barcode 80 may be placed in the field rather than provided on extraction solution bottle 65 and procurement extraction container 5. This may be more efficient when multiple units of either extraction solution bottle 65 or procurement extraction container 5 for a single donor.

Figure 3:
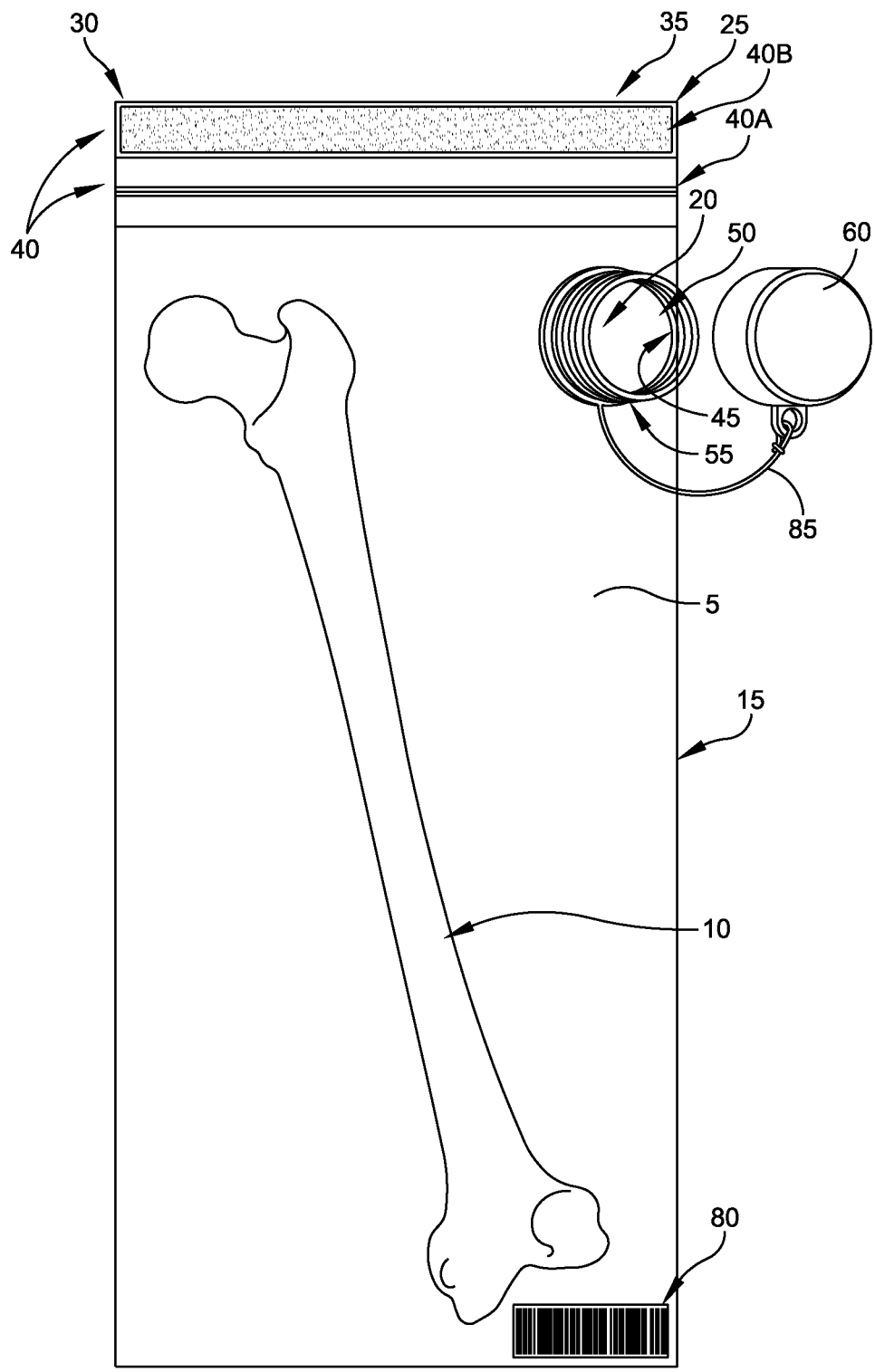
FIG. 3 illustrates another exemplary embodiment of an extraction solution bottle having a flexible retainer extending between a screw cap and a threaded connection to the bottle.

With reference to FIG. 3, and in another embodiment, a flexible retainer 85 may be configured to extend between screw cap 60 and connector interface 55. This provides an "all-in-one" solution in which the bag is a single item to minimize keeping track of a cap.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A procurement extraction container for procuring an allograft tissue and detection of contamination in the allograft tissue, the procurement extraction container comprising:

at least one wall defining an interior sized to receive an allograft tissue;

a first opening providing a first passageway between the interior and an external environment, the first opening sized to receive therethrough the allograft tissue from the external environment into the interior;

a first closure device in operable connection with the first opening, the first closure device providing a hermetic seal at the first opening so as to provide, with the at least one wall, a sterile barrier for procurement of the allograft tissue disposed within the interior;

a second opening providing a second passageway between the interior and the external environment, and the second opening having a connector interface; and a second closure device in operable connection with the connector interface of the second opening, the second closure device providing a hermetic seal at the second opening so as to provide, with the first closure and the at least one wall, the sterile barrier for procurement of the allograft tissue disposed within the interior;

wherein the second opening comprising a connector interface having both (1) a set of outwardly disposed screw threads configured to rotatably engage with the second closure device and (2) a set of inwardly disposed screw threads configured to rotatably engage with a set of outwardly disposed screw threads on a bottle containing an extraction fluid.

2. The procurement extraction container of claim 1, wherein the second closure device is a screw cap.

3. The procurement extraction container of claim 1, wherein the at least one wall includes a flexible sheet of material.

4. The procurement extraction container of claim 3, wherein the flexible sheet of material forms a plastic bag.

5. The procurement extraction container of claim 1, wherein the first closure device comprises a ziplock closure.

6. The procurement extraction container of claim 1, wherein the first closure comprises a glue bar closure.

7. The procurement extraction container of claim 6, wherein the glue bar closure includes a non-resealable glue so as to provide a one-time closure.

8. The procurement extraction container of claim 1, wherein the first closure comprises a ziplock closure and a glue bar closure.

9. The procurement extraction container of claim 1, wherein the connector interface of the second opening is a port configured for selective connection with the bottle containing the extraction fluid.

10. The procurement extraction container of claim 1, wherein the interior is sized to receive the allograft tissue of a bone together with a suitable volume of extraction fluid to detect contamination of the allograft tissue.

11. The procurement extraction container of claim 1, wherein the interior is sized to receive the allograft tissue of a soft tissue graft together with a suitable volume of extraction fluid to detect contamination of the allograft tissue.

12. The procurement extraction container of claim 1, further comprising a flexible retainer extending between the second passageway and the second closure device.

* * * * *